United States Patent [19]

Barker

[11] Patent Number: 5,548,566

[45] Date of Patent: *Aug. 20, 1996

[54] DICTATION RECORDING DEVICE HAVING MEANS FOR RAPIDLY TRANSMITTING RECORDED DICTATION TO A RECEIVING DEVICE

[76] Inventor: Bruce J. Barker, 160 Beverly Rd., South Huntington, N.Y. 11746

[*] Notice: The term of this patent shall not extend beyond the expiration date of Pat. No. 5,398,220.

[21] Appl. No.: 226,997

[22] Filed: Apr. 13, 1994

Related U.S. Application Data

[63] Continuation-in-part of Ser. No. 863,950, Apr. 6, 1992, Pat. No. 5,398,220.

[51] Int. Cl.$^6$ .................................................. G11B 19/16
[52] U.S. Cl. ............................ 369/25; 369/29; 360/61
[58] Field of Search ............................... 369/25, 29, 27, 369/28, 26, 2, 3, 4; 379/75; 360/48, 50, 61–62, 72.1, 72.2, 72.3

[56] References Cited

U.S. PATENT DOCUMENTS

| | | | |
|---|---|---|---|
| 3,560,666 | 2/1971 | Borkman | 369/7 |
| 4,377,825 | 3/1983 | Kasubuchi et al. | 360/48 |
| 4,517,424 | 5/1985 | Kroczynski | 200/52 |
| 4,605,975 | 8/1986 | Beaman | 360/62 |
| 4,758,913 | 7/1988 | Saltzman et al. | 360/72.1 |
| 5,033,077 | 7/1991 | Bergeron et al. | 379/67 |
| 5,045,327 | 9/1991 | Tarlow et al. | 381/51 |
| 5,161,199 | 11/1992 | David | 381/51 |
| 5,319,620 | 6/1994 | Hohenbuchler et al. | 369/29 |

*Primary Examiner*—Ali Neyzari

[57] ABSTRACT

A portable voice recording device has a microphone for generating an electrical microphone signal representative of an acoustic speech signal, a memory device for storing a memory signal representative of the electric signal, and an output port controller for rapidly transmitting the memory signal to a remote device at a rate greater than the rate at which the microphone signal was generated.

4 Claims, 9 Drawing Sheets

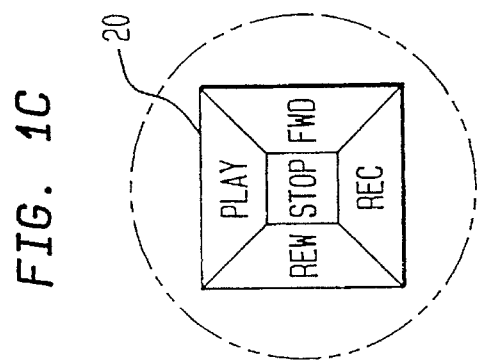
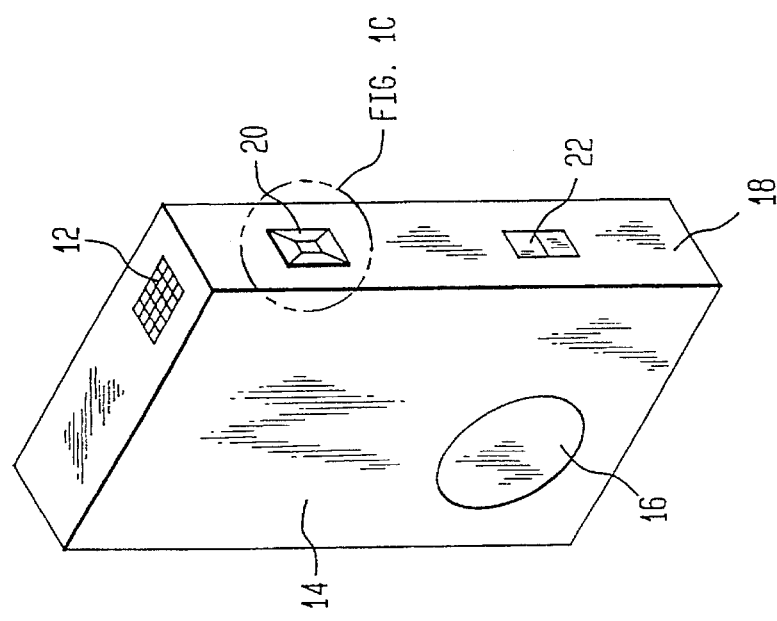
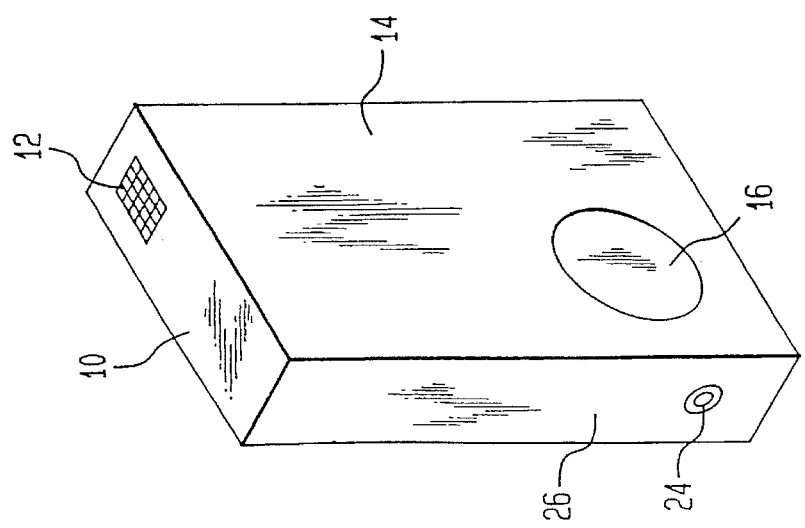

5,548,566

DICTATION RECORDING DEVICE HAVING MEANS FOR RAPIDLY TRANSMITTING RECORDED DICTATION TO A RECEIVING DEVICE

RELATED APPLICATIONS

This is a continuation-in-part of application Ser. No. 07/863,950 filed Apr. 6, 1992, now U.S. Pat. No. 5,398,220.

BACKGROUND OF THE INVENTION

The invention relates generally to dictation recording devices. Conventional dictation recording devices record a user's dictation on a magnetic tape. In response to a user's request, the device reproduces the dictation by reading the recorded signal from the tape and preparing an electric signal representative of the recorded dictation. The electric signal drives a loudspeaker which reproduces the recorded dictation.

After some dictation is recorded, the user typically provides the magnetic tape to a typist who prepares a typewritten transcript. The typist inserts the tape into a tape playing device which includes a loudspeaker for generating an acoustic reproduction of the dictation recorded on the tape. While listening to the reproduction of the dictation, the typist types a transcript of the dictation on the keyboard of a wordprocessing device.

One object of the present invention is to provide a portable dictation recording device which includes an output port for rapidly transmitting an output signal representative of the recorded dictation to a receiving device. For example, the output signal is rapidly transmitted to a speech recognition device which analyzes the output signal and automatically prepares a printed transcript of the dictation.

SUMMARY OF THE INVENTION

The invention relates to a portable voice recording device. The device includes a microphone for generating an electrical microphone signal representative of an acoustic speech signal and a memory device for storing a memory signal representative of said electric signal. It also includes an output port controller for rapidly transmitting the memory signal to a remote device at a rate greater than the rate at which the microphone signal was generated.

In another aspect, the invention includes a loudspeaker for generating an acoustic signal corresponding to the memory signal and a chassis having a size and shape which allows the chassis to fit in a user's hand, wherein the microphone, the memory device, the output port controller, and the loudspeaker are all housed within the chassis.

Other objects, features and advantages of the invention are apparent from the following description of preferred embodiments taken together with the drawings.

BRIEF DESCRIPTION OF THE DRAWINGS

FIGS. 1(a), 1(b) and 1(c) are illustrations of a hand held dictation recording device.

DESCRIPTION OF THE PREFERRED EMBODIMENT

Figure 2:
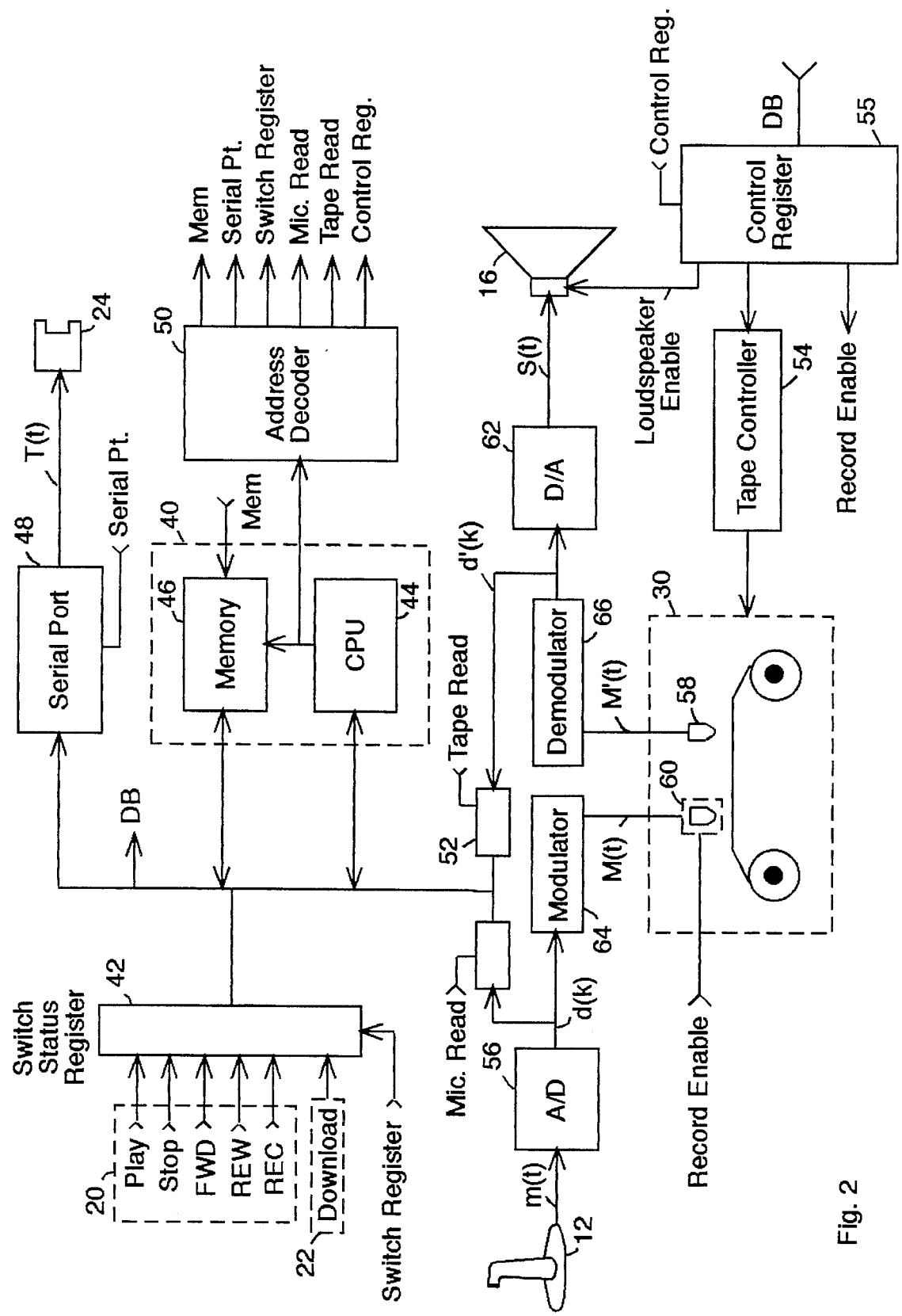
FIG. 2 is a block diagram of a portable dictation recording device according to the invention which includes a magnetic tape for storing dictation.

FIGS. 1 (a), 1(b) and 1(c) illustrate a handheld dictation recording device according to the invention. A top side 10 of the device includes a microphone 12 for receiving a person's voice and converting it to an electrical signal. As explained more fully below, the electrical signal is stored sequentially on a storage device within the dictation recording device. A front side 14 of the recording device includes a loudspeaker 16 for reproducing the stored voice signal in accordance with a user's request.

The recording device includes two input switches for accepting a user's instructions. Referring to FIG. 1(b), and 1(c) a control switch 20 is attached to a right side 18 of the device. Control switch 20 has five positions labelled "Play", "FWD", "REV", "REC", and "Stop". To select either of the "Play", "FWD", "REV", or "REC" positions, the user must press the switch to the desired position and hold. Once the user releases the switch from the selected position, the switch springs back to the Stop position.

A download switch 22 is also attached to right side 18 to allow the user to instruct the device to transmit a previously recorded message to a remote device. Toward this end, recording device includes an output port 24 attached to left side 26. In response to the assertion of switch 22, the device rapidly transmits an electrical representation of the previously recorded message to the output port 24. A computer is typically connected to the output port 24 to receive and store the transmission.

Figure 3A:
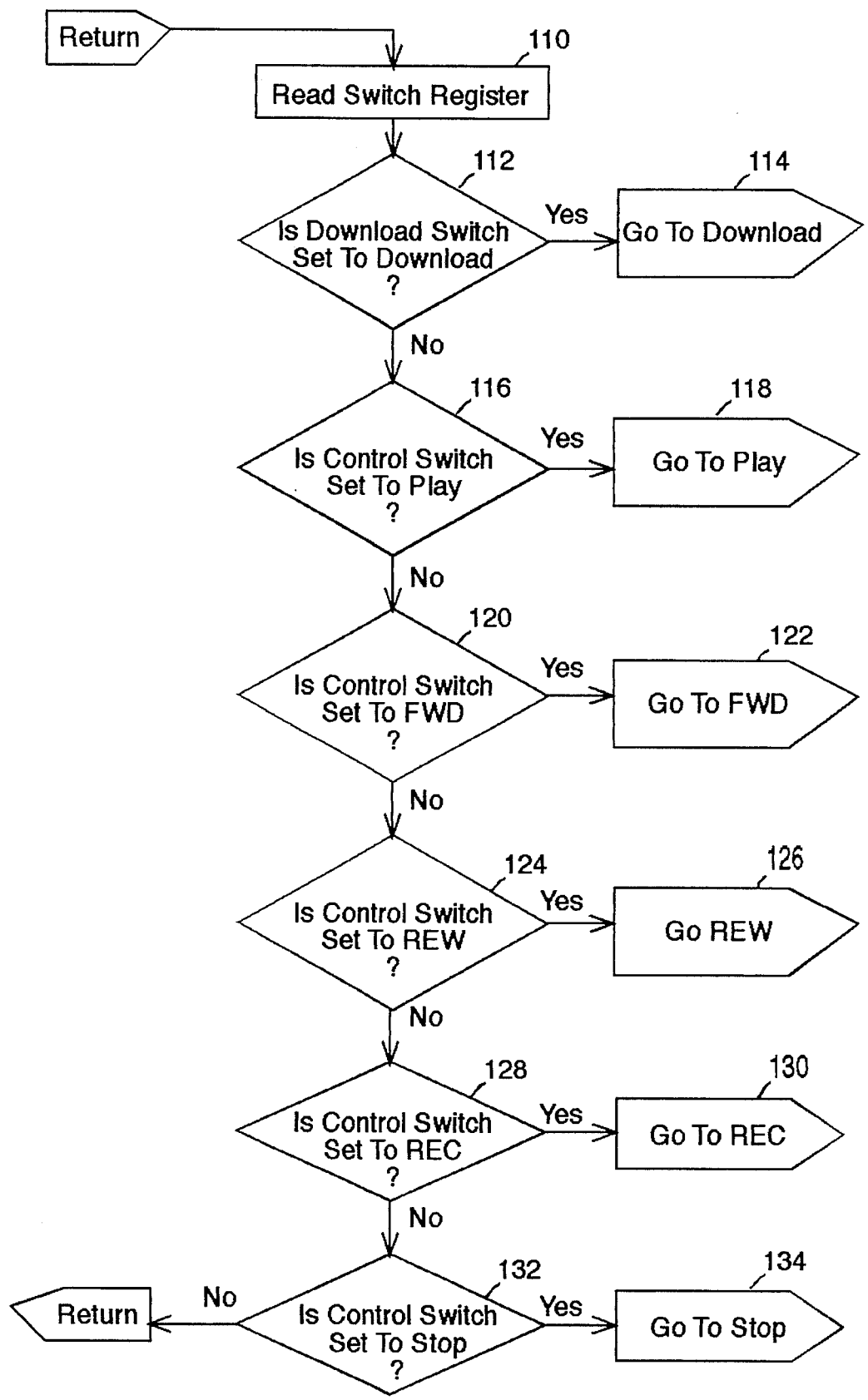
FIGS. 3(a)–3(f) are flow charts illustrating procedures for controlling the operation of a dictation recording device.
Figure 3B:
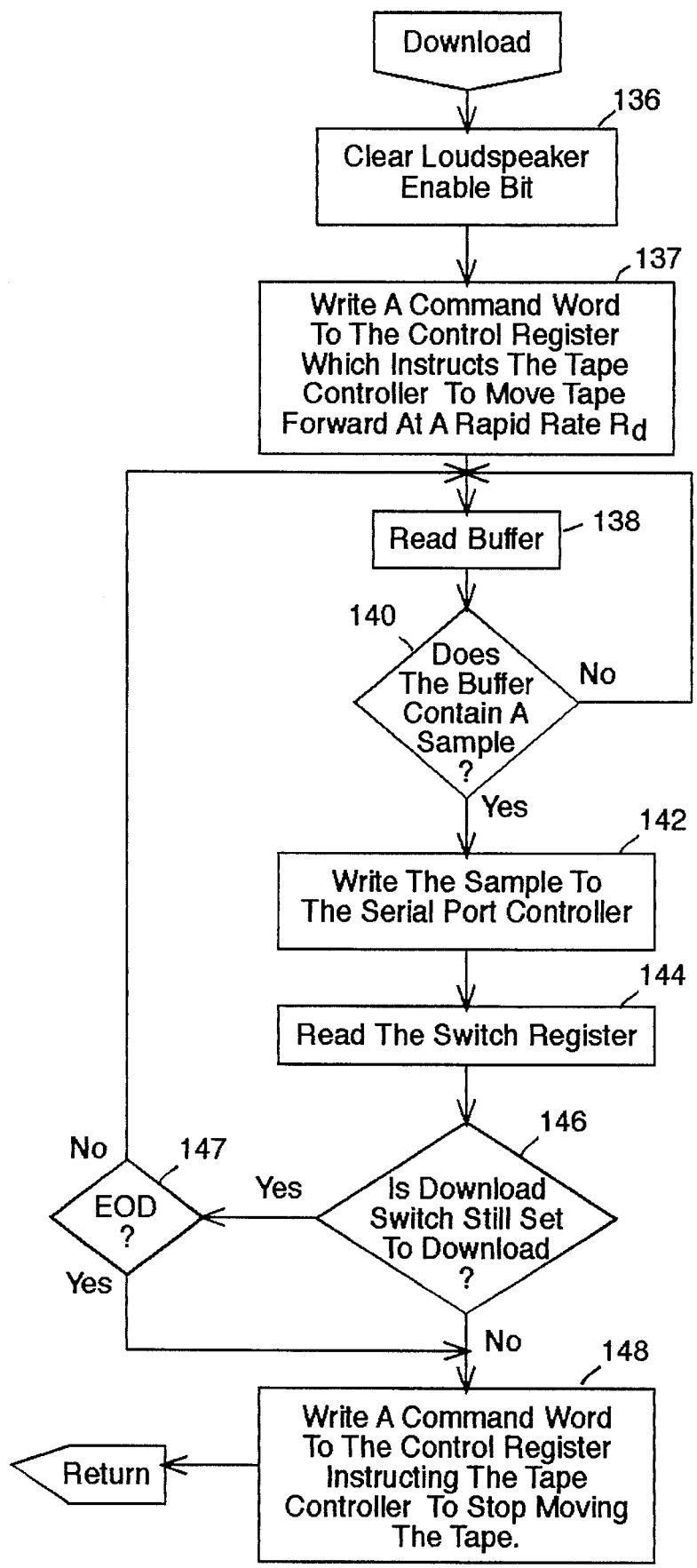
Figure 3C:
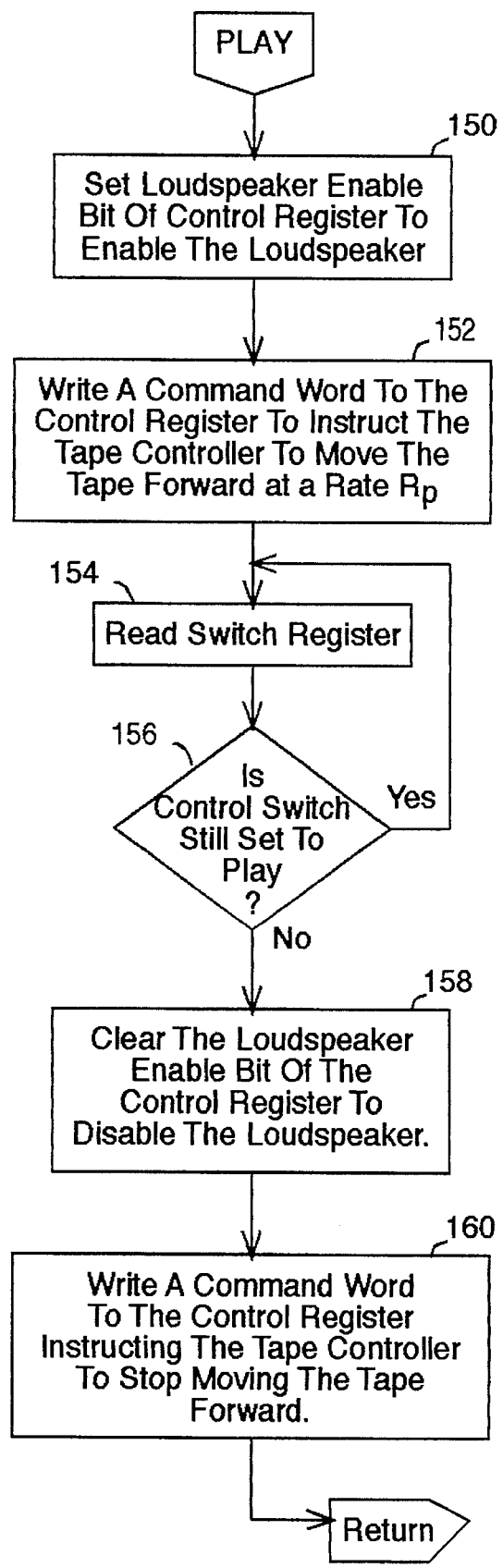
Figure 3D:
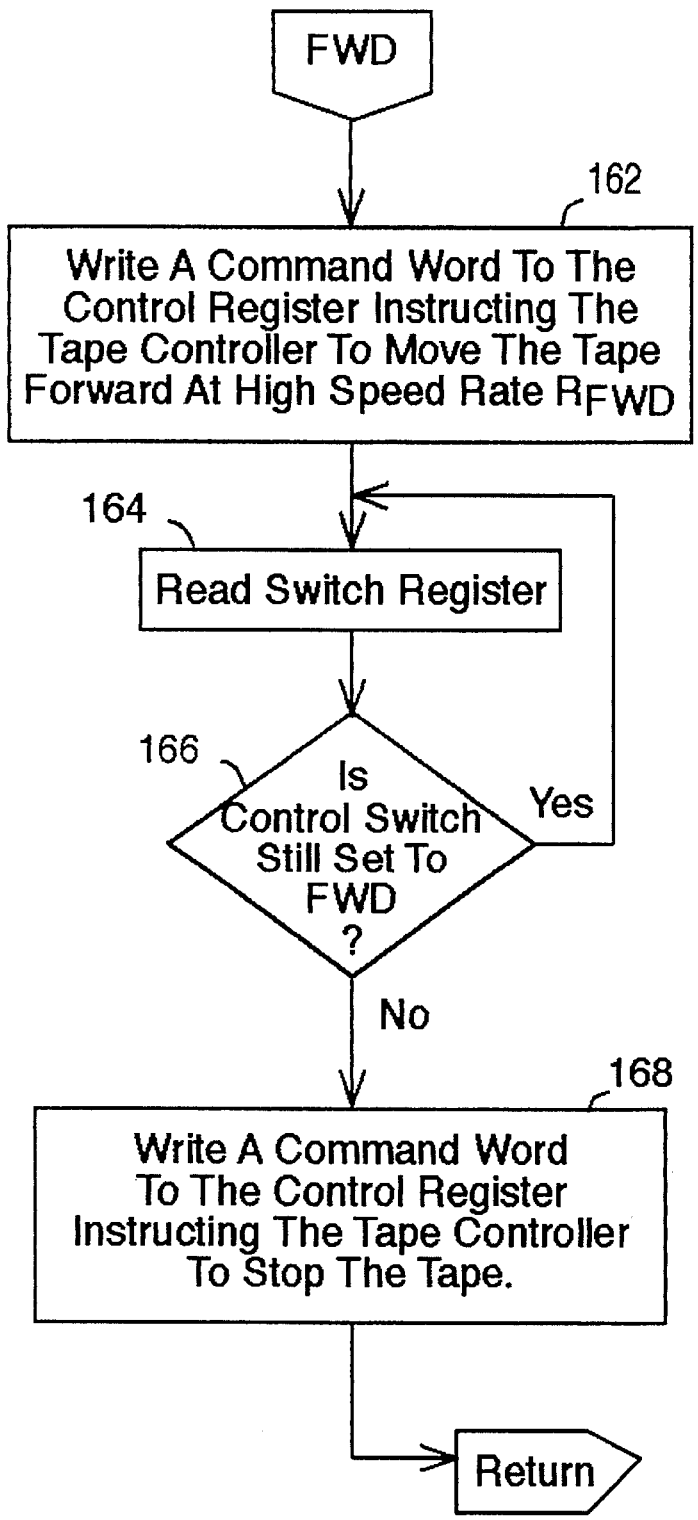
Figure 3E:
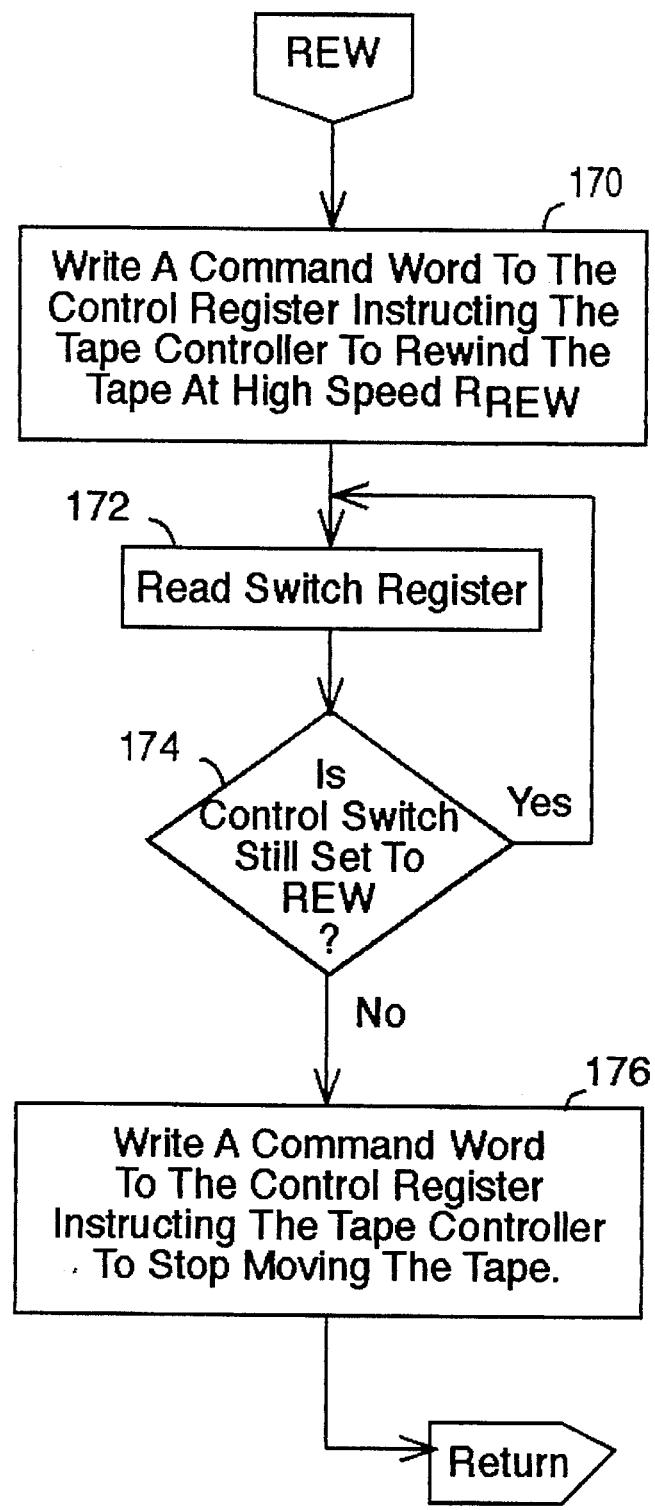

Referring to FIG. 2, in one embodiment, the storage device is a magnetic tape cassette 30 having a pair of reels 32, 34 for holding a magnetic tape 36. A controller 40 monitors the status of switches 20, 22. More specifically, the controller 40 includes a central processor unit (CPU) 44 and a memory 46. The memory stores a program which is executed by CPU 44 to direct the operation of the recording device. To determine the status of the switches, the program directs CPU 44 to read a switch status register 42 whose content indicates the status of the switches. (Step 110) (FIG. 3(a). Based on the status of the switches, the program directs CPU 44 to implement the desired operation specified by the status of the switches. (Steps 112–132)

Referring to FIGS. 2, 3(a), and 3(c)–3(g), the following describes the operation of the device while download switch 22 is in the normal position. If, during this normal mode, the control switch 20 is asserted to the REC position, the CPU implements a Record routine. (Steps 128, 130, 178–188), (FIG. 3(f). In accordance with the record routine, the CPU writes a sequence of command words to a control register 55. (Steps 178, 180, 186, 188). During the CPU's write cycle, an Address Decoder 50 decodes the address and asserts a Control Reg signal which instructs the control register to accept a command from a data bus DB.

The CPU's first command sets a Record Enable bit within the control register to enable the write head 60. (Step 178). The CPU then sets a bit of the command register which instructs the tape controller to rotate the reels of cassette 30 forward causing the tape to unwind from supply reel 32, pass beneath a write head 60, and collect on take up reel 34, at a rate $R_{rec}$. (Step 180). As the tape travels beneath the write head 60, the microphone 12 provides an electrical representation m(t) of the user's voice to a analog to digital converter A/D 56. A/D 56 digitizes the microphone signal at a sampling rate SR, to produce a digitized signal d(k).

A/D 56 provides each sample of the digitized signal d(k) to a modulator 64. The modulator generates an analog modulation signal M(t) representative of the samples of the digitized signal. The modulation signal M(t) is provided to write head 60 which converts the modulated signal to a corresponding magnetic signal m'(t). Thus, as the tape passes beneath the write head, the magnetic signal m'(t) is recorded on the tape.

The CPU then repeatedly reads the switch register 42 to determine if the control switch is still asserted to the REC position. (Steps 182, 184). As soon as the switch register indicates that the the switch is no longer in the REC position, the CPU clears the Record enable bit within the control register 55 to disable write head 60. (Step 186). It then instructs the tape controller to stop moving the tape forward. (Step 188).

Figure 3:
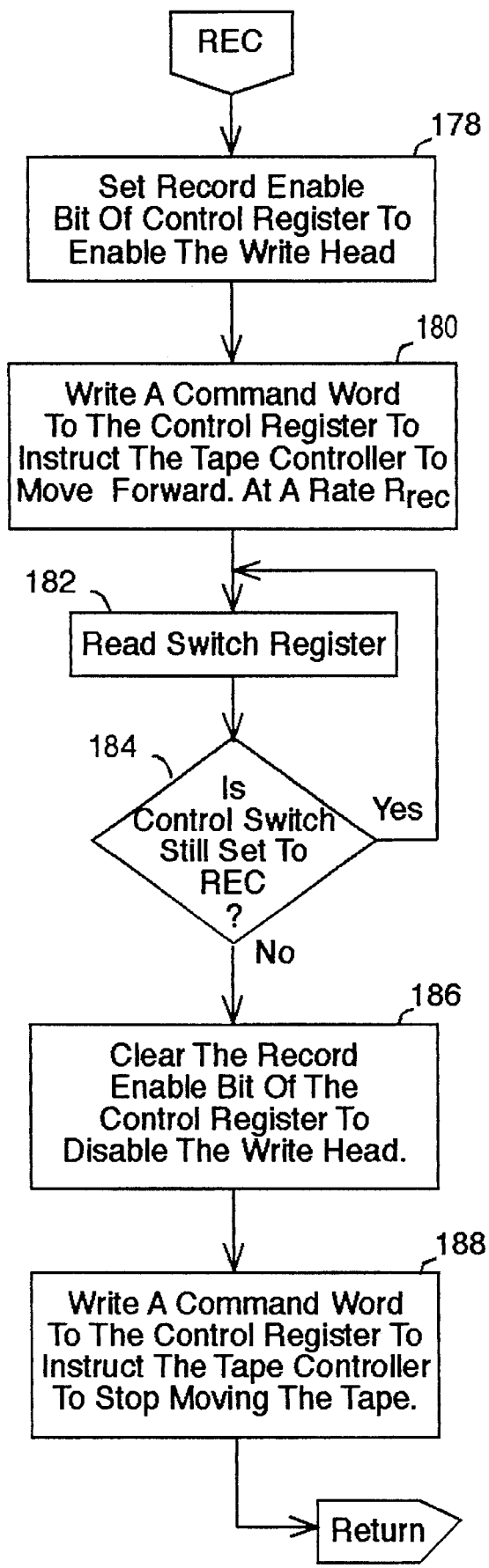

If the user desires to modify his previously recorded dictation, he first presses the REW button. In response, CPU 44 implements the Rewind routine. (Steps 124, 126, 170–176), (FIG. 3(*e*). In accordance with the Rewind routine, the CPU instructs tape controller 54 to rotate the reels of the tape at high speed in a reverse direction. (Step 170). The CPU then repeatedly reads the status of the switch register 42 to determine if the control switch is still asserted to the REW position. (Steps 172, 174). As soon as the switch register indicates that the the switch is no longer in the REW position, the CPU instructs the tape controller to stop moving the tape forward. (Step 176).

To determine if the tape has reached a desired location, the user releases the control switch 20 from the REW position and presses the switch to its Play position. In response, CPU 44 implements a Play routine. (Steps 116,118, 150–160), (FIG. 3(*c*)). In accordance with the play routine, the CPU sets a loudspeaker enable bit in the control register 50 to enable the loudspeaker 16. (Step 150). It then commands the tape controller to rotate the reels of casette 30 forward at a rate $R_p$. (Step 152). As the tape moves forward, a read head 58 senses the magnetic signal m'(t) recorded on the tape and generates a corresponding analog electrical signal M'(t). The signal M'(t) is provided to a demodulator 66 which demodulates the analog signal to generate samples of a reproduced digitized signal d'(k). The samples of the digitized signal d'(k) are then provided to a digital to analog converter A/D 62 which converts the samples to an analog electrical signal S(t). S(t) is applied to the loudspeaker 16 which, in response, reproduces the recorded dictation.

The CPU then repeatedly reads the status of the switch register 42 to determine if the control switch is still asserted to the Play position. (Steps 154, 156). As soon as the switch register indicates that the the switch is no longer in the Play position, the CPU clears the loudspeaker enable bit within the control register 55 to disable the loudspeaker. (Step 158). It then instructs the tape controller to stop moving the tape forward. (Steps 158, 160).

By listening to the loudspeaker reproduce the previously recorded dictation, the user can itemtively search for a desired target point on the tape by rewinding the tape and playing it back as needed. If he rewinds the tape too far, he presses the switch to its FWD position. In response, the CPU implements a FWD routine. (Steps 120, 122,162–168), (FIG. 3(*d*)). In accordance with the FWD routine, the CPU instructs the tape controller to rotate the reels forward at a high speed. (Step 162). When the user releases the switch from the FWD position, the CPU instructs the tape controller to stop the tape at its current position. (Steps 164–168).

Once the user locates the desired target point on the tape for modification, he presses control switch 20 to its REC position and begins dictating the new material. The new material is recorded on the tape in the same manner as described above, starting at the selected target point on the tape.

To transfer the recorded dictation to a remote device, the user connects the remote device to the output port 24 and asserts download switch 22 to its download position. Upon recognizing that the download switch is asserted, CPU 44 implements a Download routine. (Steps 112,114, 136–148), (FIG. 3(*b*)).

In accordance with the download routine, the CPU clears the loudspeaker enable bit to assure that the loudspeaker 16 is disabled. (Step 136). It then directs tape controller 54 to turn the reels 32, 34 forward at a relatively rapid rate $R_d$ (e.g., rate $R_d$ is greater than the rates $R_p$ and/or $R_{rec}$, preferably substantially greater) to commence reading the dictation recorded on tape 36. (Step 137). As explained above, the demodulator 66 converts the tape signal into digital samples d'(k). A tape read buffer 52 temporarily stores the samples. CPU 44 reads each sample from the buffer 52 by reading from an address assigned to the buffer. (Step 138). The address decoder 50 responds to the address by asserting an Tape Read Reg signal which instructs the buffer to provide the oldest sample on the data bus DB. CPU 44 forwards the sample received from the buffer 52 to a serial port controller 48. (Step 142). Serial Port controller 48 encodes the sample d'(k) into a transmission signal T(t). It then provides the signal T(t) to the output port 24 for transmission to the remote device. The remote device is typically a computer which includes a decoder for decoding the transmitted signal back into the digital samples d'(k). The computer then performs desired processing on the digital samples.

The samples are provided to the serial port controller 48 at a rapid rate to allow the controller to transmit the recorded dictation at a rate substantially greater than the rate at which the microphone provided the original dictation. Thus, the user can transfer even a long speech to the remote device very quickly, e.g., much more quickly than the time it took to record the dictation.

The CPU continues reading samples from buffer 52 and forwarding them to serial port 48 until either the download switch is deasserted or until the tape contains no additional dictation. (Steps 138, 140, 144, 146, 147). It then instructs the tape controller to stop moving the tape forward. (Step 148). To determine whether the tape contains additional dictation (Step 147), the CPU maintains a running measure of the average energy of the samples d'(k). If the average energy has been below a threshold T for at least a period of time P (e.g., 10 sec.), the CPU concludes that the tape has no additional dictation.

Figure 4:
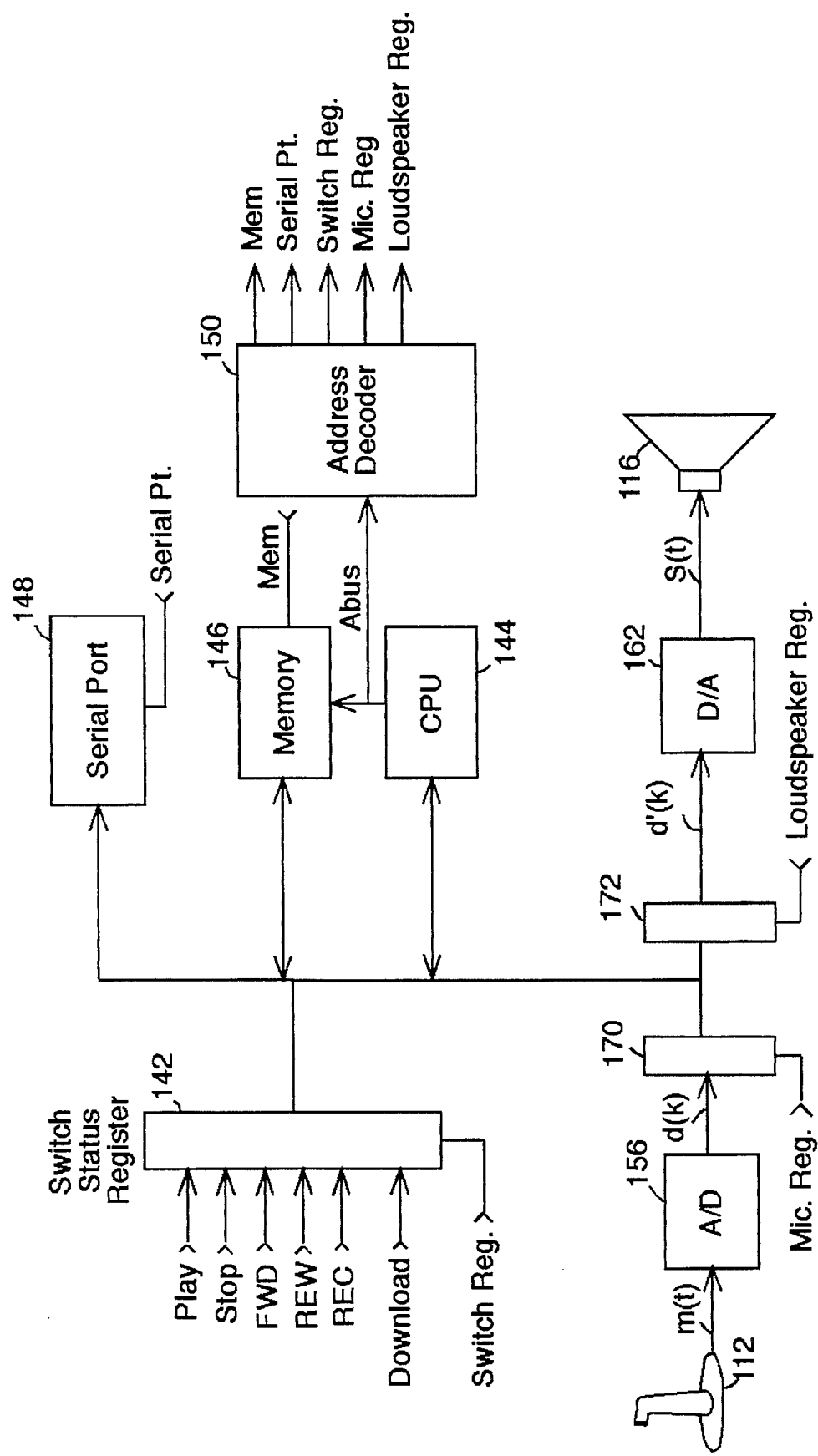
FIG. 4 is a block diagram of a dictation recording device according to the invention which includes a digital memory for storing dictation.

Referring to FIG. 4., in another embodiment, the storage device is a digital memory device such as CMOS random access memory 146. As in the previously described embodiment, a CPU 144 controls the device by repeatedly reading from a switch status register 142 to determine the status of the switches 20, 22. While switch 20 in the REC position, a microphone 112 provides a microphone signal m(t) to a digital to analog converter A/D 156. A/D 156 digitizes the microphone signal to produce a corresponding digital signal d(k). It supplies each sample to a microphone register 170 for temporary storage. The CPU 144 reads each sample from the register 170 by reading from an address assigned to the register. A decoder 150 decodes the address and asserts a control signal Mic Reg which instructs register 170 to provide a sample d(k) on a data bus DB. CPU 144 receives the sample d(k) from bus DB and stores it in a corresponding location in memory 146.

Toward this end, CPU 144 writes the sample d(k) to an address assigned to the location in memory. Decoder 150 decodes the address and asserts a MEM control signal instructing memory 146 to load the data from data bus DB into a location identified by the address asserted by CPU 144 on an address bus Abus.

After transferring a sample from register 170 to memory, CPU 144 again reads the Status Register 142 to determine the status of the switches. If switch 20 is still in the REC position, CPU 144 reads the next sample of d(k) and stores it in memory 146 as described above.

Once CPU 144 detects that switch 20 is in the play position, it begins reading samples of d(k) from memory 146 and writing them to a loudspeaker buffer 172 at a rate $R_p$. Buffer 172 provides the samples to an A/D converter 162 which converts the sample to a corresponding analog signal S(t). S(t) drives loudspeaker 116 to reproduce the recorded dictation.

Once CPU 144 detects that switch 22 is in the download position, it begins reading samples of d(k) from memory 146 and writing them to serial port controller 148 at a relatively rapid rate $R_d$, e.g., faster than the rate $R_p$. As described above, the serial port controller 148 encodes the sample d(k) into a transmission signal T(t) and transmits the signal T(t) to the output port 24.

Like the previously described embodiment, this embodiment transmits the samples at a rapid rate to allow the user to transfer the recorded dictation at a rate greater than the rate at which the dictation was originally recorded.

While the invention has been described in conjunction with preferred embodiments, it is evident that numerous alternatives, modifications, variations and uses will be apparent to those skilled in the art in light of the foregoing description. For example, the recorded dictation could be transmitted using any technique for transmission. As another example, the dictation could be processed by the recording device before transmission to the remote device.

What is claimed is:

1. A portable voice recording device comprising:

a microphone for generating an electrical signal representative of an acoustic speech signal, memory device for storing a memory signal representative of said electric signal, and an output port controller for transmitting said memory signal to a voice processing computer device at a rate substantially more rapid than the rate at which said electrical signal was generated.

2. The portable voice recording device of claim 1 further comprising a loudspeaker for generating an acoustic signal corresponding to said memory signal.

3. The portable voice recording device of claim 1 further comprising a chassis having a size and shape which allows said chassis to fit in a user's hand, wherein said microphone, said memory device and said output port controller are all housed within said chassis.

4. A portable voice recording device comprising:

a microphone for generating an electrical signal representative of an acoustic speech signal, memory device for storing a memory signal representative of said electric signal, and an output port controller for transmitting said memory signal to a voice processing computer device at a rate substantially more rapid than the rate at which said electrical signal was generated, a loudspeaker for generating an acoustic signal corresponding to said memory signal; and a chassis having a size and shape which allows said chassis to fit in a user's hand, wherein said microphone, said memory device, said output port controller, and said loudspeaker are all housed within said chassis.

* * * * *